(12) United States Patent
Ueno

(10) Patent No.: US 10,702,687 B2
(45) Date of Patent: Jul. 7, 2020

(54) MICRONEEDLE UNIT

(71) Applicant: TOPPAN PRINTING CO., LTD., Taito-ku (JP)

(72) Inventor: Hisami Ueno, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 250 days.

(21) Appl. No.: 15/416,093

(22) Filed: Jan. 26, 2017

(65) Prior Publication Data

US 2017/0128708 A1    May 11, 2017

Related U.S. Application Data

(63) Continuation of application No. PCT/JP2015/070428, filed on Jul. 16, 2015.

(30) Foreign Application Priority Data

Jul. 30, 2014  (JP) .................................. 2014-154970

(51) Int. Cl.
*A61M 37/00*    (2006.01)

(52) U.S. Cl.
CPC ... *A61M 37/0015* (2013.01); *A61M 2037/003* (2013.01); *A61M 2037/0023* (2013.01); *A61M 2037/0046* (2013.01)

(58) Field of Classification Search
CPC .................. A61M 2037/0023; A61M 37/0015
See application file for complete search history.

(56) References Cited

U.S. PATENT DOCUMENTS

| 7,789,733 | B2 | 9/2010 | Sugimura et al. |
| 8,292,696 | B2 | 10/2012 | Sugimura et al. |
| 8,377,364 | B2 | 2/2013 | Shiomitsu et al. |
| 8,506,980 | B2 | 8/2013 | Takada |
| 8,876,575 | B2 | 11/2014 | Sugimura et al. |
| 9,238,384 | B2 | 1/2016 | Shiomitsu et al. |
| 2008/0195035 | A1* | 8/2008 | Frederickson ....... A61K 9/0021 604/22 |
| 2008/0262444 | A1 | 10/2008 | Takada |

(Continued)

FOREIGN PATENT DOCUMENTS

| JP | 3152532 U | 8/2009 |
| JP | 2009-254876 A | 11/2009 |

(Continued)

OTHER PUBLICATIONS

International Search Report dated Oct. 20, 2015 in PCT/JP2015/070428, filed Jul. 16, 2015.

*Primary Examiner* — Deanna K Hall
(74) *Attorney, Agent, or Firm* — Oblon, McClelland, Maier & Neustadt, L.L.P.

(57) ABSTRACT

A microneedle unit including a microneedle including a substrate having a first surface and a second surface opposite to the first surface, the microneedle further including a projection protruding from the first surface of the substrate, an adhesive sheet including a sticking region attached to the second surface, the adhesive sheet further including an adhesive region protruding outside the substrate from the sticking region in a direction parallel to the second surface, and a protective sheet covering a portion of the adhesive region outside of the substrate in the direction parallel to the second surface.

20 Claims, 5 Drawing Sheets

(56) References Cited

U.S. PATENT DOCUMENTS

2009/0131887 A1 5/2009 Shiomitsu et al.
2010/0256568 A1* 10/2010 Frederickson .... A61M 37/0015
 604/173

FOREIGN PATENT DOCUMENTS

| JP | 2013-066730 A | 4/2013 |
| WO | WO 2006/080508 A1 | 8/2006 |
| WO | WO 2008/004597 A1 | 1/2008 |

* cited by examiner

MICRONEEDLE UNIT

CROSS-REFERENCE TO RELATED APPLICATIONS

The present application is a continuation of International Application No. PCT/JP2015/070428, filed Jul. 16, 2015, which is based upon and claims the benefits of priority to Japanese Application No. 2014-154970, filed Jul. 30, 2014. The entire contents of these applications are incorporated herein by reference.

BACKGROUND OF THE INVENTION

Field of the Invention

The present invention relates to microneedle units having a microneedle used for drug administration.

Discussion of the Background

Drug administration using a microneedle is known as a method of administration of a drug into the body. The microneedle includes a plurality of projections having a needle-shape formed on the surface of a substrate. In the administration method using a microneedle, the substrate is pressed against the skin so that the projections puncture the skin to form holes, through which a drug is delivered into the body (e.g., see PTLs 1 to 3).
PTL 1: WO 2006/080508
PTL 2: WO 2008/004597
PTL 3: JP-A-2009-254876

SUMMARY OF THE INVENTION

According to one aspect of the present invention, a microneedle unit includes a microneedle including a substrate having a first surface and a second surface opposite to the first surface, the microneedle further including a projection protruding from the first surface of the substrate, an adhesive sheet including a sticking region attached to the second surface, the adhesive sheet further including an adhesive region protruding outside the substrate from the sticking region in a direction parallel to the second surface, and a protective sheet covering a portion of the adhesive region outside of the substrate in the direction parallel to the second surface.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
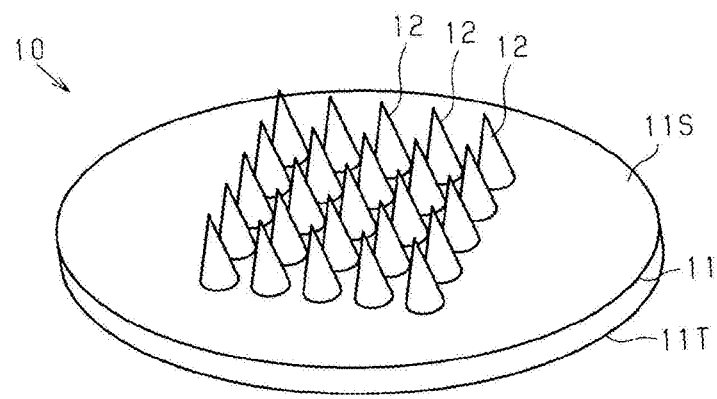
FIG. 1 is a perspective view which shows a perspective structure of a microneedle included in a microneedle unit according to an embodiment.

The embodiments will now be described with reference to the accompanying drawings, wherein like reference numerals designate corresponding or identical elements throughout the various drawings.
With reference to FIGS. 1 to 13, an embodiment of a microneedle unit will be described.

Configuration of Microneedle

Figure 2:
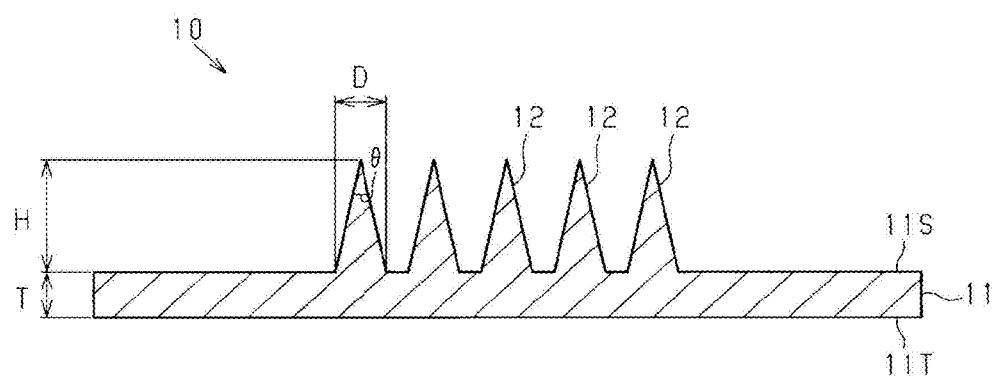
FIG. 2 is a cross sectional view which shows a cross sectional structure of a microneedle included in a microneedle unit according to an embodiment.

With reference to FIGS. 1 and 2, a configuration of a microneedle 10 included in the microneedle unit will be described.
As shown in FIG. 1, the microneedle 10 includes a plate-shaped substrate 11 and a projection 12 protruding from the substrate 11. The substrate 11 has a first surface 11S on which the projections 12 are formed and a second surface 11T which is a surface opposite from the first surface 11S.
The outline of the substrate 11 as seen in the direction perpendicular to the first surface 11S is not specifically limited, and may be a circle, oval or rectangle.
The projection 12 may be a pyramid or cone shape. Further, the projection 12 may be a shape which does not have a pointed tip, for example, a cylinder or prism shape. Further, the projection 12 may be a shape composed of a combination of two or more three dimensional shapes, for example, a cone stacked on a cylinder. In other words, the projection 12 may be any shape that can pierce the skin. Moreover, the projection 12 may have a narrow portion or roughness on a side wall.
The number of projections 12 is not specifically limited, but one or more. When the microneedle 10 includes a plurality of projections 12, each of the plurality of projections 12 may be arranged regularly or irregularly on the first surface 11S of the substrate 11. For example, the plurality of projections 12 is arrayed in a matrix or concentric pattern.

As shown in FIG. 2, the projection 12 has a length H in the thickness direction of the substrate 11, that is, a length from the first surface 11S to the tip of the projection 12 in a direction perpendicular to 11) the first surface 11S. The length H of the projection 12 is determined depending on the purpose of puncture made by the projection 12, the type of drug administered, and a depth of the hole of the puncture required to be made by the projection 12. Preferably, the length H of the projection 12 is in the range of 20 μm or more and 1000 μm or less.

When the puncture target is the human skin and the depth of the hole of the puncture made by the projection 12 is a length that passes through the stratum corneum and does not reach the nerve plexus, the length H of the projection 12 is preferably in the range of 200 μm or more and 700 μm or less, more preferably in the range of 200 μm or more and 600 μm or less.

When the depth of the hole is in such a range that it penetrates the stratum corneum and does not reach nerve plexus, the drug can be delivered to a site deeper than the stratum corneum. Since the hole formed in the stratum corneum closes as time elapses, the stratum corneum serves as a barrier to the outside so that the drug delivered deeper than the stratum corneum is held in the body. Accordingly, the drug can be held in the body for a long period of time since the drug is prevented from being peeled off due to the metabolism of the stratum corneum or washing the skin for skin care or the like.

Moreover, when the depth of the hole is in such a range that it is located in the stratum corneum, the length H of the projection 12 is preferably in the range of 30 μm or more and 300 μm or less, more preferably in the range of 30 μm or more and 250 μm or less, and further more preferably in the range of 30 μm or more and 200 μm or less.

Since the depth of the hole is in a range that reaches the stratum corneum, the drug can be retained in the stratum corneum. The drug in the stratum corneum is excreted from the body as the time elapses since the stratum corneum is constantly newly produced by metabolism. Accordingly, a state in which the drug is retained in the body can be easily released, for example, by washing the skin or peeling the skin.

When the microneedle 10 includes a plurality of projections 12, the length H of the plurality of projections 12 may be the same or different from each other. For example, in the case where the length H of the projections 12 located on the outer periphery area among the plurality of projections 12 is larger than the length H of the projections 12 located in the center area, the projections 12 can be easily in contact with a curved surface of the skin when the skin of the administration target is a curved surface. Alternatively, for example, in the case where the length H of the projection 12 located on the outer periphery area among the plurality of projections 12 is smaller than the length H of the projection 12 located in the center area, the projections 12 located on the outer periphery area, which are susceptible to an external force, may have an improved mechanical strength.

The projection 12 has a width D, which is a maximum length of the projection 12 in a direction parallel with the first surface 11S of the substrate 11. The width D of the projection 12 is determined depending on the required aspect ratio of the projection 12 or the required volume of the hole. Preferably, the width D of the projection 12 is in the range of 1 μm or more and 300 μm or less. For example, when the projection 12 has a regular quadrangular pyramid or regular quadrangular prism shape, the width D of the projection 12 is a diagonal length of a square which is the bottom of the projection 12, that is, the bottom which is in contact with the first surface 11S of the substrate 11. Further, for example, when the projection 12 has a cone or cylinder shape, the width D of the projection 12 is a diameter of a circle which is the bottom of the projection 12 which is in contact with the first surface 11S of the substrate 11.

When the tip of the projection 12 is formed in a pointed shape and the hole of the puncture is formed to penetrate the stratum corneum, the tip angle θ of the projection 12 is preferably in a range of 5° or more and 45° or less, more preferably in a range of 8° or more and 25° or less.

The tip angle θ of the projection 12 is a maximum angle made by the tip of the projection 12 in a cross section perpendicular to the first surface 11S of the substrate 11. For example, when the projection 12 has a regular quadrangular pyramid shape, the tip angle θ of the projection 12 is an apex angle of a triangle having a diagonal line of a square of the bottom of the projection 12 as a base and the apex of the regular quadrangular pyramid projection 12 as an apex.

The substrate 11 has a thickness T which is a length from the first surface 11S to the second surface 11T in a cross section perpendicular to the first surface 11S of the substrate 11. The thickness T of the substrate 11 is not specifically limited.

In the above configuration, a length of the microneedle 10 in an extending direction of the projection 12, that is, in the thickness direction of the substrate 11 is the sum of the length H of the projection 12 and the thickness T of the substrate 11.

Further, the shape of the projection 12 is not limited to the shape above described, and may be appropriately determined depending on the purpose of puncture made by the projection 12 or the type of drug administered. For example, the purpose of puncture made by the projection 12 may be promotion of percutaneous absorption of the drug or extraction of a substance in the body to the outside the body through the skin. Further, the shape of the projection 12 can be determined in view of improvement in piercing performance to the skin.

The microneedle 10 is preferably made of a biocompatible material. The biocompatible material has a little effect on the body, and includes a water soluble polymer, water insoluble polymer, biopolymer, metal, resin and the like.

The biocompatible material may be a known material. Examples of the biocompatible material include alginates, curdlan, chitin, chitosan, glucomannan, polymalic acid, collagen, collagen peptide, hydroxypropyl cellulose, gelatin, silicon, titanium, silicone, polylactic acid, polyglycolic acid and the like. Although there is no clear distinction between chitin and chitosan, chitin with deacetylation of 70% or more is generally referred to as chitosan. Deacetylation may be performed by a known technique. Chitin, chitosan, and chitosan derivatives having biocompatibility may be substances originating from crustaceans such as crab and shrimp, substances originating from the myceliums or microorganism generated plants, or substances using these as starting materials. Chitosan, chitin or chitosan, and chitin or chitosan derivatives are preferable as a forming material of the microneedle 10 since they provide a beauty effect on the skin as well as sterilization effect and antimicrobial effect.

The administration method using the microneedle 10 is not specifically limited. For example, a drug may be applied on the surface of the projections 12 so that the drug is delivered into the skin when the projections 12 pierce the skin. Alternatively, a drug may be contained in the projections 12 so that the drug is delivered into the skin when the projections 12 are dissolved while being pierced into the skin. Further, a liquid drug may be applied on the skin before or after the microneedle 10 is pierced into the skin so that the drug is delivered into the skin through the holes formed by the projections 12. In addition, drug administration may also be performed by a combination of these methods.

The type of the drug is not specifically limited as long as it works when administered into the skin, and may be, for example, physiologically active agents or cosmetic compositions having aesthetic effect. Further, when an aromatic substance is used as a drug, a fragrance is imparted to the microneedle 10 to thereby obtain the microneedle 10 suitable for use as a beauty product. Moreover, the drug may include biologics. Biologics are drugs which use a raw material or material derived from cells or cell tissues of a human or an animal.

As described above, the drug may be applied on the surface of the projection, contained in the projection 12, applied on the skin, or used in the form of a combination thereof depending on the method of administration.

Further, the substrate 11 and the projection 12 may be made of a material having the same composition, or materials having different compositions. In the configuration in which the substrate 11 and the projection 12 are made of a material having the same composition, the substrate 11 and the projection 12 can be easily integrally formed.

The microneedle 10 can be manufactured by using various known techniques. For example, when a resin is used as a material for the microneedle 10, the microneedle 10 can be manufactured by injection molding, extrusion molding, imprinting, hot embossing, casting or the like. Further, the microneedle 10 can be manufactured by machining such as cutting or by etching. Alternatively, an original plate of the microneedle may be formed to produce an intaglio plate having a reversed pattern of raised and recessed portions of the original plate by plating or by molding of a resin and thereby reproduce the microneedle 10 by using the produced intaglio plate.

Configuration of Microneedle Unit

With reference to FIGS. 3 to 13, a configuration of a microneedle unit having the above microneedle 10 will be described.

Figure 3:
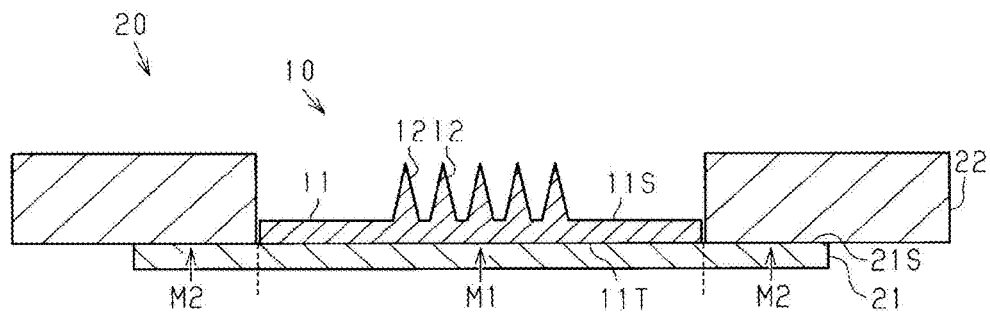
FIG. 3 is a cross sectional view which shows an example of cross sectional structure of a microneedle unit according to an embodiment.

As shown in FIG. 3, a microneedle unit 20 includes the microneedle 10, an adhesive sheet 21 and a protective sheet 22.

The adhesive sheet 21 has an adhesive surface 21S, which is one of two surfaces of the adhesive sheet 21. The adhesive sheet 21 is attached to the substrate 11 with the adhesive surface 21S oriented to the second surface 11T of the substrate 11 of the microneedle 10. A portion of the adhesive surface 21S extends outside the substrate 11 in a plane direction which is parallel to the second surface 11T of the substrate 11. That is, the adhesive surface 21S of the adhesive sheet 21 includes a sticking region M1 which is a region attached to the second surface 11T of the substrate 11 and an adhesive region M2 which protrudes outside the substrate 11 from the sticking region M1 in the plane direction.

The material forming the adhesive surface 21S is preferably a biocompatible material. The adhesive surface 21S has an adhesive force that can hold the microneedle 10 and hold the adhesive sheet 21 to be attached to the administration target for a long period of time.

The protective sheet 22 covers the adhesive region M2 of the adhesive surface 21S. The protective sheet 22 is attached to the adhesive sheet 21 in a manner to be removable from the adhesive sheet 21 by a force applied by a user by holding and pulling the protective sheet 22. Preferably, the forming material of the protective sheet 22 is a material having an adhesive force that can hold the adhesive sheet 21 to be attached to the administration target for a long period of time and that ensures a non-biocompatible material not to remain on the adhesive surface 21S when the protective sheet 22 is peeled off from the adhesive sheet 21.

The thickness of the protective sheet 22 is preferably longer than the length of the microneedle 10 in the thickness direction of the substrate 11, that is, the sum of the length H of the projection 12 and the thickness T of the substrate 11. According to this configuration, the top surface of the protective sheet 22 is located higher than the tip of the projection 12, thereby preventing the projection 12 from being touched by a human hand or other members. Further, the microneedle units 20 can be stacked in the thickness direction of the protective sheet 22 without damaging the projections 12 even if the projections 12 are not protected by another member. Accordingly, the microneedle unit 20 can be easily handled and managed. In the above configuration, a difference between the thickness of the protective sheet 22 and the sum of the length H of the projection 12 and the thickness T of the substrate 11 is preferably in a range of 0.2 mm or more and 3.0 mm or less.

Figure 4:
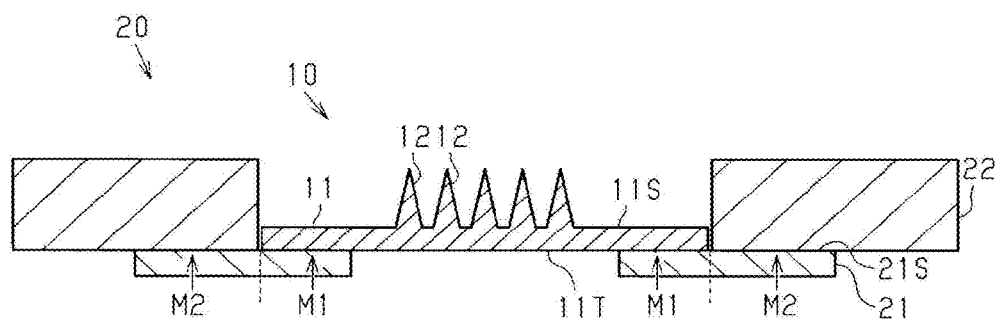
FIG. 4 is a cross sectional view which shows an example of cross sectional structure of a microneedle unit according to an embodiment.

Further, the sticking region M1 on the adhesive surface 21S of the adhesive sheet 21 may be provided on the entire surface of the second surface 11T of the substrate 11 of the microneedle 10 as shown in FIG. 3, or alternatively, may be provided on a portion of the surface of the second surface 11T, for example, on the outer peripheral region of the second surface 11T as shown in FIG. 4.

Figure 5:
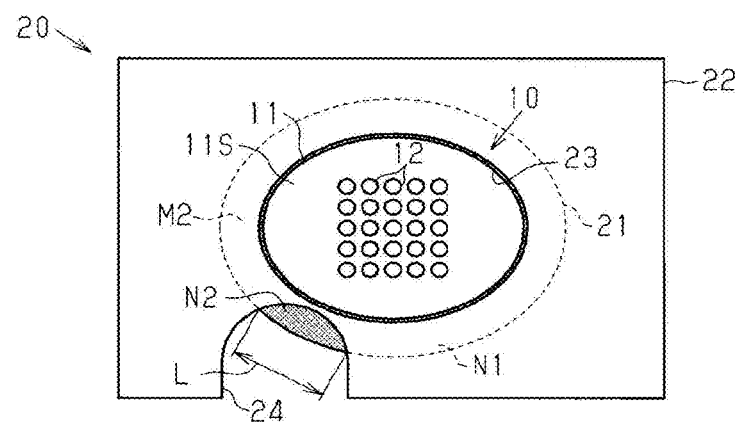
FIG. 5 is a plan view which shows an example of a planar structure of a microneedle unit according to an embodiment.

As shown in FIG. 5, an opening 23 is formed in a center region of the protective sheet 22. The opening 23 corresponds to a first opening. The microneedle 10 is disposed in the region in which the opening 23 is formed such that the first surface 11S of the substrate 11 and the projections 12 are exposed from the opening 23. The outline of the opening 23 as seen in the direction perpendicular to the first surface 11S of the substrate 11 of the microneedle 10 is not specifically limited, and may be any shape as long as it is larger than the outline of the substrate 11. However, from the point of view of improvement in function of the protective sheet 22 to protect the adhesive surface 21S, the outline of the opening 23 is preferably a similar shape to the outline of the substrate 11, and a difference in the size of the region in which the opening 23 is formed and the size of the substrate 11 is preferably small. In addition, the outline of the protective sheet 22 as seen in the direction perpendicular to the first surface 11S of the substrate 11 is not specifically limited.

The outline of the adhesive sheet 21 as seen in the direction perpendicular to the first surface 11S of the substrate 11 is not specifically limited as long as the adhesive region M2 is formed. The outline of the adhesive sheet 21 may be or may not be a similar shape to the outline of the substrate 11 of the microneedle 10. The adhesive region M2 has a size that can hold the adhesive sheet 21, which holds the microneedle 10, to be attached to the administration target for a desired period of time. Further, the adhesive region M2 may be disposed to surround the entire circumference of the outer peripheral edge of the substrate 11, or the adhesive region M2 may protrude outside the outer peripheral edge of the substrate 11 from a portion of the outer peripheral edge.

The protective sheet 22 covers a portion of the adhesive region M2, and the adhesive region M2 includes a covered region N1 covered by the protective sheet 22 and an exposed region N2 which is not covered by the protective sheet 22. The adhesive surface 21S of the adhesive sheet 21 is exposed from the protective sheet 22 in the exposed region N2.

For example, in the example shown in FIG. 5, a window 24 is formed in the protective sheet 22 of a rectangular outline shape by removing a portion of the protective sheet 22. The window 24 corresponds to a second opening. A portion of the adhesive region M2 in which the window 24 is formed in the protective sheet 22, that is, a portion which overlaps a notched region at the position of the window 24, forms the exposed region N2. In other words, the exposed region N2 is a region of the adhesive region M2 which is exposed from the window 24. The outer peripheral edge of the protective sheet 22 is recessed inside at a position where the window 24 is formed, and an area of the notched region of the protective sheet 22 at the position of the window 24 is larger than that of the exposed region N2. That is, the adhesive region M2 overlaps part of the region notched at the position of the window 24, and part of the outer peripheral edge of the adhesive sheet 21 is exposed from the window 24.

A length of the longest line segment among the line segments connecting any two points on the outer peripheral edge of the exposed region N2 and extending through the exposed region N2 is a maximum length L of the exposed region N2. The maximum length L is preferably 7 mm or more. Further, the exposed region N2 is preferably smaller than the covered region N1. In other words, the area of the exposed region N2 is preferably less than 50% of the area of the adhesive region M2.

Effects

Effects of the microneedle unit 20 according to the present embodiment will be described.

As described above, since the adhesive surface 21S of the adhesive sheet 21 includes the exposed region N2, a user of the microneedle unit 20 can peel the protective sheet 22 from the adhesive sheet 21 starting from near the exposed region N2 while supporting the adhesive sheet 21 at the exposed region N2. For example, the user picks a portion of the adhesive sheet 21 in which the exposed region N2 is formed from upper and lower sides with fingers of one hand, and holds the protective sheet 22 by the other hand to peel off the protective sheet 22 from the adhesive sheet 21. Then, the user presses the microneedle 10 against a desired site on the skin while holding the portion in which the exposed region N2 is formed to stick the adhesive region M2 of the adhesive sheet 21 onto the skin.

In this configuration, the user can easily peel off the protective sheet 22 since a starting point for peeling of the protective sheet 22 can be easily provided compared with the configuration in which the entire adhesive region M2 is covered by the protective sheet 22, and the user does not need to change a position to hold the microneedle unit 20 before, during or after peeling of the protective sheet 22. As a result, an excessively large force due to peeling of the protective sheet 22 can be prevented from acting on each part of the microneedle unit 20. Accordingly, deterioration of functions of the microneedle unit 20 can be reduced.

Further, when an area of the exposed region N2 is larger than a size that can be supported by a center portion of a human finger, the user can easily support the exposed region N2. From this point of view, a maximum length L of the exposed region N2 is preferably 7 mm or more as described above. On the other hand, when the exposed region N2 is smaller than the covered region N1, an area of the exposed region N2 is not excessively large and an appropriate size of the covered region N1 is provided. Accordingly, excessive decrease in protection function of the adhesive surface 21S due to the protective sheet 22 can be prevented.

Further, since the window 24 is formed in a region which includes the outer peripheral edge of the protective sheet 22, the user can easily support the exposed region N2.

The opening 23 and the window 24 may or may not be connected to each other. As shown in FIG. 5, when the exposed region N2 has a sufficient area, the projections 12 can be prevented from being touched by the user's hand when the user supports the exposed region N2 in the configuration in which the opening 23 and the window 24 are not connected to each other, that is, the opening 23 and the window 24 are separated from each other by the protective sheet 22.

Figure 6:
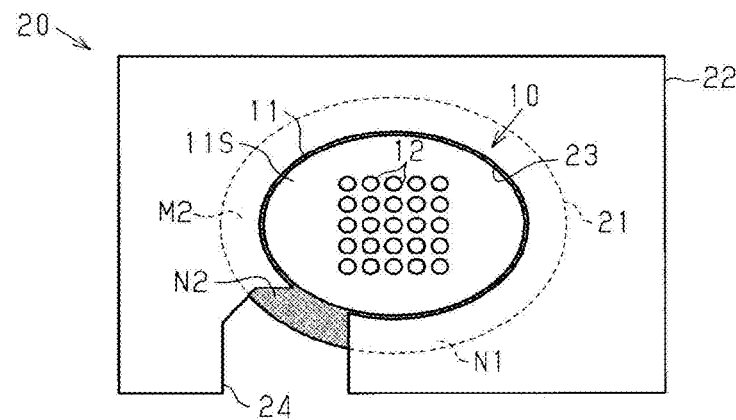
FIG. 6 is a plan view which shows an example of a planar structure of a microneedle unit according to an embodiment.

On the other hand, the protective sheet 22 can be easily produced, that is, the microneedle unit 20 can be easily produced in the configuration in which the opening 23 and the window 24 are connected to each other as shown in FIG. 6.

Figure 7:
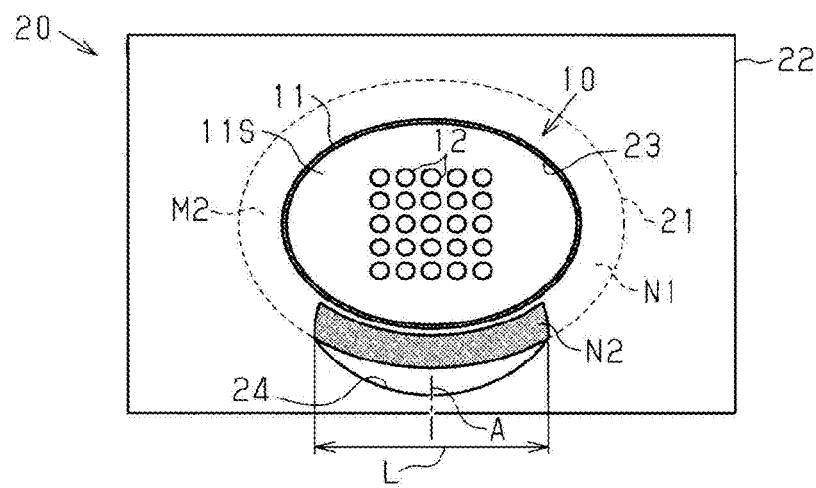
FIG. 7 is a plan view which shows an example of a planar structure of a microneedle unit according to an embodiment.
Figure 8:
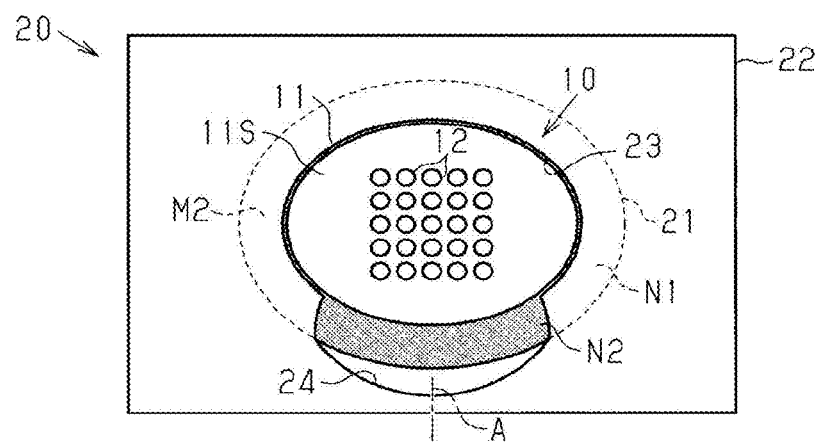
FIG. 8 is a plan view which shows an example of a planar structure of a microneedle unit according to an embodiment.

As shown in FIG. 7, the window 24 may be shaped not to reach the outer peripheral edge of the protective sheet 22, for example, as a through hole which penetrates the protective sheet in a circular hole or an oval hole shaped to follow the outline of a fingertip. In this configuration, for example, the user picks a portion of the adhesive sheet 21 in which the exposed region N2 is formed from upper and lower sides with fingers by inserting a finger into the window 24 from the underside of the protective sheet 22, and peels off the protective sheet 22 from the adhesive sheet 21 while supporting the exposed region N2. Accordingly, the user can easily peel off the protective sheet 22. In this configuration as well, the opening 23 and the window 24 may or may not be connected to each other. FIG. 7 shows a configuration in which the opening 23 and the window 24 are not connected to each other, and FIG. 8 shows a configuration in which the opening 23 and the window 24 are connected to each other.

In the above configuration, as indicated by the alternate long and short dash line A, an incision can be formed on the protective sheet 22 at a position between the edge of the window 24 and the outer peripheral edge of the protective sheet 22 so that the protective sheet 22 is cut off at this position. In this configuration, since the user can easily support the exposed region N2 by inserting a finger into the window 24 and a degree of freedom in movement of the protective sheet 22 is improved, the user can easily peel off the protective sheet 22.

Further, in a configuration in which the window 24 does not to reach the outer peripheral edge of the protective sheet 22, the protective sheet 22 may be partially folded back to the side opposite to the adhesive sheet 21 when the user supports the exposed region N2. With reference to FIGS. 9 to 12, these configurations will be described.

Figure 9:
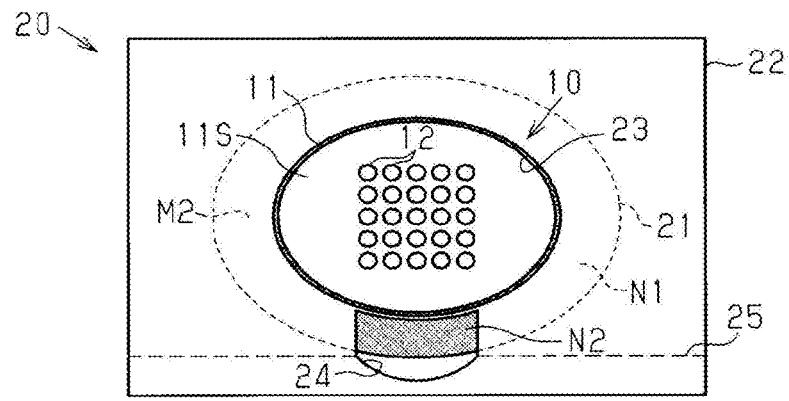
FIG. 9 is a plan view which shows an example of a planar structure of a microneedle unit according to an embodiment.

As shown in FIG. 9, a weakened portion 25 is formed on the protective sheet 22 in a region between the edge of the window 24 and the outer peripheral edge of the protective sheet 22. The weakened portion 25 is formed as a straight line connecting two points on the outer peripheral edge of the protective sheet 22. The weakened portion 25 is, for example, a portion having a perforation or a portion having a reduced thickness of the protective sheet 22 by providing a groove on a surface of the protective sheet 22 facing the adhesive sheet 21. A mechanical strength of the weakened portion 25 is lower than that of the portion other than the weakened portion 25 on the protective sheet 22. According to this configuration, the protective sheet 22 can be folded back at the weakened portion 25 to the side opposite to the adhesive sheet 21. Preferably, the weakened portion 25 linearly extends from a position on the edge of the window 24 which overlaps the outer peripheral edge of the adhesive sheet 21.

Figure 10:
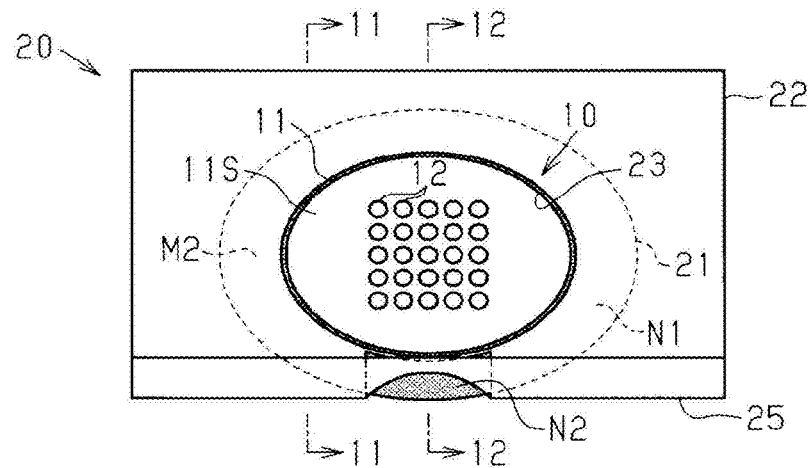
FIG. 10 is a plan view which shows an example of a planar structure of a microneedle unit according to an embodiment, showing that a protective sheet is folded back.

As shown in FIG. 10, when the protective sheet 22 is peeled off, the protective sheet 22 is folded back at the weakened portion 25 to the side opposite to the adhesive sheet 21. As a result, a portion of the exposed region N2 is located on the end of the microneedle unit 20.

Figure 11:
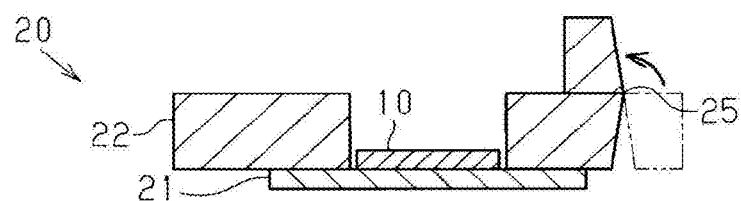
FIG. 11 is a cross sectional view which shows an example of a cross sectional structure of a microneedle unit according to an embodiment, and the cross sectional structure is taken along the line 11-11 of FIG. 10.
Figure 12:
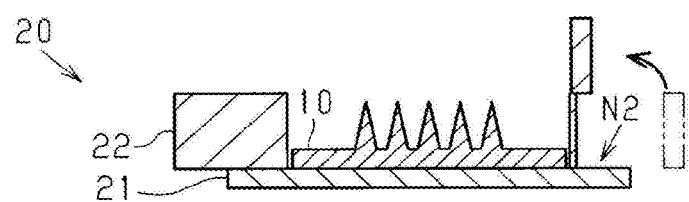
FIG. 12 is a cross sectional view which shows an example of a cross sectional structure of a microneedle unit according to an embodiment, and the cross sectional structure is taken along the line 12-12 of FIG. 10.

FIGS. 11 and 12 are cross sectional views of the microneedle unit 20 in a state in which the protective sheet 22 is folded back. FIG. 11 shows a cross sectional view at a position where the exposed region N2 is not located, and FIG. 12 shows a cross sectional view at a position where the exposed region N2 is located. In FIGS. 11 and 12, the protective sheet 22 before being folded back is indicated by the alternate long and two short dashed lines.

As shown in FIG. 11, the protective sheet 22 is folded back at the weakened portion 25 to the side opposite to the adhesive sheet 21. Since the mechanical strength of the weakened portion 25 is lower than that of the portion other than the weakened portion 25 on the protective sheet 22, the user can easily fold back the protective sheet 22 at the weakened portion 25.

As shown in FIG. 12, as a result of folding back of the protective sheet 22, a portion of the exposed region N2 is located on the end of the microneedle unit 20. Accordingly, the user can easily support the exposed region N2. Accordingly, the protective sheet 22 can be further easily peeled off.

Further, in the above configuration, when the protective sheet 22 is folded back, a portion of the exposed region N2 exposed from the protective sheet 22 which has been folded back at the end of the microneedle unit 20 preferably has a maximum length of 7 mm or more. The maximum length is a length of the longest line segment among the line segments connecting any two points on an outer peripheral edge of the portion exposed from the protective sheet 22 which has been folded back and extending through the exposed portion. In this case, the maximum length L of the exposed region N2 is 7 mm or more, as a matter of course.

Figure 13:
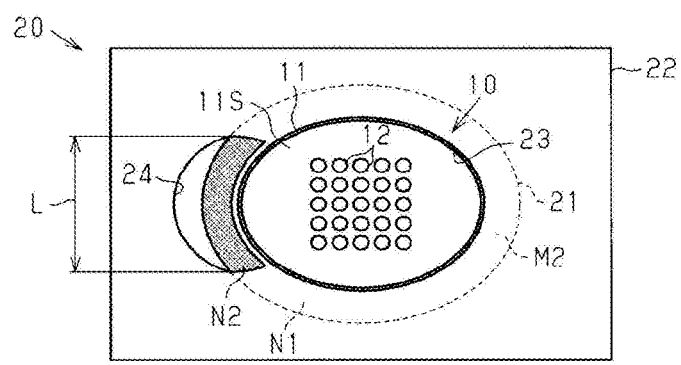
FIG. 13 is a plan view which shows an example of a planar structure of a microneedle unit according to an embodiment.

As shown in FIG. 13, the exposed region N2 may be located in a region of the adhesive region M2 having a length extending in one direction, that is, the longitudinal direction, which is relatively small. For example, the exposed region N2 may be located in a region perpendicular to a longitudinal axis of the adhesive region M2 when the outline of the adhesive region M2 is an oval shape, or in a region along a short side of a rectangular shape when the outline of the adhesive region M2 is a rectangular shape. In the above configuration, the opening 23 and the window 24 may or may not be connected to each other.

Further, as shown in FIG. 7, the configuration in which the exposed region N2 is located in a region of the adhesive region M2 having a length extending in one direction, which is relatively long, is advantageous in that the maximum length L of the exposed region N2 can be increased As described above, according to the microneedle unit of the present embodiment, advantageous effects listed below can be achieved.

(1) Since the adhesive surface 21S of the adhesive sheet 21 includes the exposed region N2, a starting point for peeling of the protective sheet 22 can be easily formed near the exposed region N2. Accordingly, the protective sheet 22 can be easily peeled. Further, since the window 24 is formed in the protective sheet 22 such that the exposed region N2 is formed by the adhesive region M2 exposed from the window 24, the exposed region N2 is easily provided in the adhesive region M2.

(2) Since the starting point for peeling of the protective sheet 22 is provided near the exposed region N2, a manufacturer of the microneedle unit 20 can use the position of the exposed region N2 to guide a user to use the microneedle unit 20 in a manner intended by the manufacturer. That is, the manufacturer can guide a user to peel the protective sheet 22 from a point intended by the manufacturer and to stick the microneedle unit 20 onto the skin from a point intended by the manufacturer. In particular, appropriate guidance can be made when the outline of the microneedle 10 is not a circular shape, such as an oval shape or rectangular shape.

The user can use the microneedle unit 20 according to the above guidance. Accordingly, the user can use the microneedle unit 20 in the easy-to-use manner intended by the manufacturer, and easily apply the microneedle 10 on the skin.

Further, according to the above guidance, the position supported by the user when peeling the protective sheet 22 is decided so that the user does not need to change a position to hold the adhesive sheet 21 when the user sticks the adhesive sheet 21 onto the skin. Since the adhesive surface 21S of the adhesive sheet 21 can be prevented from inadvertently sticking on the finger of the user, the adhesive sheet 21 along with the microneedle 10 can be stuck on the skin while the adhesive surface 21S holds a sufficient adhesive force. Accordingly, the adhesive sheet 21 is held to be stuck on the skin of the administration target, that is, the projections 12 of the microneedle 10 is held to be pierced into the skin for a sufficient period of time. As a result, the effect of administration by the microneedle 10 can be easily obtained.

(3) Since the exposed region N2 is smaller than the covered region N1, more than half of the adhesive region M2 is covered by the protective sheet 22. Accordingly, an excessive decrease in protective function of the adhesive region M2 due to the protective sheet 22 can be avoided while achieving easy peeling of the protective sheet 22.

(4) Since the maximum length L of the exposed region N2 is 7 mm or more, the exposed region N2 may have a size that can be supported by a center portion of a human finger. Accordingly, the user can easily support the exposed region N2 by using the finger, which allows for easy peeling of the protective sheet 22.

(5) Since the thickness of the protective sheet 22 is larger than the length of the microneedle 10 in the thickness direction of the substrate 11, the projections 12 can be prevented from being touched by a human hand or other members. Further, when the microneedle units 20 are stacked in the thickness direction of the protective sheet, the projections 12 are not damaged even if the projections 12 are not protected by another member. Accordingly, the microneedle unit 20 can be easily handled and managed.

Modified Example

The above embodiment can be implemented with modifications as described below.

The exposed region N2 of the adhesive sheet 21 may be formed to protrude outside the covered region N1 in the plane direction of the adhesive surface 21S. That is, the outline of the exposed region N2 in the adhesive region M2 may bulge outwardly as seen in the direction perpendicular to the first surface 11S of the substrate 11 of the microneedle 10. In this case, the exposed region N2 has an area larger than required in order to hold the adhesive sheet 21 supporting the microneedle 10 to be attached on the administration target for a desired period of time. According to this configuration, a long length can be provided for the maximum length L of the exposed region N2.

The outline of the window 24 and the outline of the exposed region N2 are not limited to those described in the above embodiment. As long as the exposed region N2 is formed by the protective sheet 22 covering a portion of the adhesive region M2, the starting point for peeling of the protective sheet 22 can be easily formed compared with the configuration in which the protective sheet 22 covers the entire adhesive region M2. Accordingly, the protective sheet 22 can be easily peeled. Further, the adhesive region M2 may be formed to entirely overlap the region in which the window 24 is formed, that is, the region of the protective sheet 22 which is notched for the window 24 so that the region in which the window 24 is formed and the exposed region N2 have the same size. However, when the adhesive region M2 partially overlaps the region in which the window 24 is formed, that is, the exposed region N2 is smaller than the region in which the window 24 is formed, a portion of the outer peripheral region of the adhesive sheet 21 is exposed from the window 24. Accordingly, the starting point of peeling of the protective sheet 22 can be more easily formed.

The microneedle unit 20 may be used in combination with a protective film for the projections 12, a case for housing the microneedle unit 20 or the like.

Figure 14:
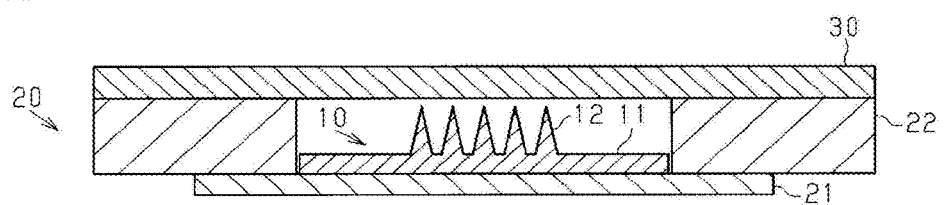
FIG. 14 is a cross sectional view which shows a cross sectional structure of a microneedle unit according to an embodiment, showing that the protective film is mounted on the microneedle unit.

For example, as shown in FIG. 14, the protective film 30 may be laminated on the protective sheet 22 on the surface opposite from the adhesive sheet 21. Accordingly, the projections 12 of the microneedle 10 can be particularly protected from the outside.

Figure 15:
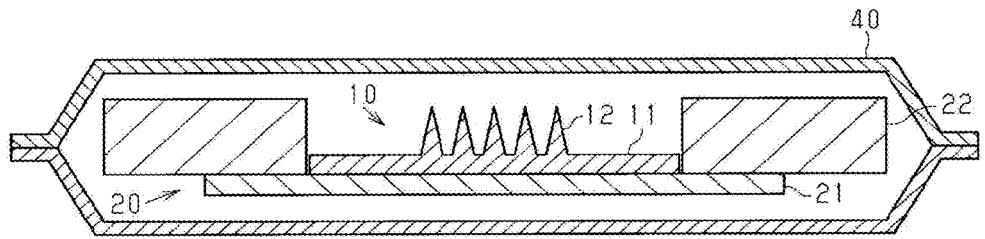
FIG. 15 is a cross sectional view which shows a cross sectional structure of a microneedle unit according to an embodiment, showing that the microneedle unit is housed in a case.

For example, as shown in FIG. 15, the entire microneedle unit 20 can be housed in a case 40. The case may be in the form of a bag or box. Accordingly, the entire microneedle unit 20 can be protected from the outside.

EXAMPLES

The above microneedle unit will be described by using specific examples and comparative examples.

Example 1

Manufacturing of Microneedle Unit

Step 1. Manufacturing of Intaglio Plate

First, an original plate for a microneedle was fabricated by micromachining. Silicon substrate was used for a forming material of the original plate in which 100 projections were arrayed in a 10-row by 10-column matrix with a pitch of 1 mm. Each projection was formed in a regular quadrangular pyramid (height: 200 μm, bottom: 38 μm×38 μm). The 100 projections were disposed in a square region, each side of which had a length of approximately 9 mm.

Then, ethylene and vinyl acetate copolymer resin was used to transfer the shape of the projections of the original plate to thereby fabricate the intaglio plate having a reversed pattern of raised and recessed portions of the original plate.

Step 2. Preparation of Material Solution for Microneedle

Then, a material solution for the microneedle was prepared. After hydroxypropyl cellulose was dissolved in water, the solution was deaerated under a vacuum environment to prepare a material solution for the microneedle. The percentage of hydroxypropyl cellulose to the material solution was 5 wt %.

Step 3. Forming of Microneedle

Then the material solution for the microneedle prepared in Step 2 was supplied to the intaglio plate fabricated in Step 1 by an ink jet method so that the recessed portion is filled with the material solution. After the intaglio plate in which the material solution was filled was left under room temperature and normal humidity for drying the material solution, a molded product was removed from the intaglio plate to obtain a microneedle. The obtained microneedle had the substrate with a thickness of 200 μm and the projections with a length of 200 μm. In this microneedle, the outline of the substrate was formed in a circular shape having a diameter of φ12 mm so that the region in which the projections were formed was located in a center portion.

Step 4. Production of Adhesive Sheet

Then, an adhesive sheet was produced. An adhesive sheet for skin patch having an adhesive surface on one of two surfaces of the sheet and having a thickness of 200 μm was formed in a 20 mm×20 mm square to thereby obtain an adhesive sheet.

Step 5. Production of Protective Sheet

Then, a protective sheet was produced. A sheet having a peelable layer with a fluorine treatment on one of two surfaces of the sheet and having a thickness of 600 μm was formed in a 30 mm×30 mm square. Subsequently, an opening was formed by removing a circular region of a diameter of φ13 mm in a center portion of the sheet, and a window was formed by removing a rectangular region having a size of 10 mm×10 mm square at one of four corners of the sheet to thereby obtain a protective sheet.

Step 6. Bonding of adhesive sheet and microneedle

Then, the second surface of the substrate of the microneedle fabricated in Step 3 was bonded to a center portion of the adhesive surface of the adhesive sheet fabricated in Step 4. The adhesive surface was exposed from the entire outer peripheral edge of the substrate outwardly in a plane direction of the substrate to form an adhesive region.

Step 7. Bonding of Protective Sheet and Adhesive Sheet

Then, the peelable layer surface of the protective sheet fabricated in Step 5 was bonded to the adhesive region of the adhesive sheet on which the microneedle fabricated in Step 6 was bonded. When the protective sheet was bonded to the adhesive sheet, the positions of the opening and the microneedle were aligned so that the microneedle protrudes from the opening of the protective sheet. Thus, the microneedle unit of Example 1 was obtained.

In the microneedle unit of Example 1, the adhesive region of 5×5 mm square on the adhesive surface of the adhesive sheet was exposed from the window of the protective sheet. The exposed region in the adhesive sheet had a maximum length of 7.1 mm.

Evaluation Result

The protective sheet was easily peeled off from the adhesive sheet by picking the protective sheet near the exposed region by using the thumb and forefinger of the right hand while picking the adhesive sheet including the exposed region by using the thumb and forefinger of the left hand. Moreover, the protective sheet was peeled off without touching the projections of the microneedle.

Comparative Example

Manufacturing of Microneedle Unit

Steps 1 to 3. Manufacturing of Microneedle

The microneedle having the same shape as that of Example 1 was obtained by the same steps as Steps 1 to 3 of Example 1. The thickness of the substrate was 200 µm, the length of the projection was 200 µm, and the outline of the substrate was a circle with a diameter of φ12 mm.

Step 4. Production of Adhesive Sheet

The adhesive sheet having the same configuration as that of Example 1 was obtained by the same step as Step 4 of Example 1. The thickness of the adhesive sheet was 200 µm, and the size of the adhesive sheet was 20 mm×20 mm square.

Step 5. Production of Protective Sheet

The protective sheet having the same configuration as that of the Example 1 except for not having the window was produced by the same step as Step 5 of Example 1 except for not forming the window. The thickness of the protective sheet was 600 µm, the opening was a circular region with a diameter of φ13 mm, the size of the protective sheet was 30 mm×30 mm square, and the window was not formed.

Steps 6 and 7. Bonding of Adhesive Sheet, Microneedle and Protective Sheet

The microneedle was bonded to the adhesive sheet, and the protective sheet was bonded to the adhesive region of the adhesive sheet by the same steps as Steps 6 and 7 of Example 1. Thus, the microneedle unit of Comparative example was obtained.

In the microneedle unit of Comparative example, the adhesive region of the adhesive sheet did not have an exposed region exposed from the protective sheet.

Evaluation Result

The protective sheet was attempted to be peeled off from the adhesive sheet by picking the protective sheet by using the thumb and forefinger of the right hand while picking the adhesive sheet by using the thumb and forefinger of the left hand. However, since there was no exposed region of the adhesive sheet, a starting point for peeling needed to be formed by pressing the nail against the adhesive sheet. Consequently, peeling of the protective sheet was very difficult. In addition, when the nail was pressing against the adhesive sheet, the outer peripheral portion of the adhesive sheet was partially folded and the adhesive surfaces were stuck each other, which made the peeling of the protective sheet difficult.

Example 2

Manufacturing of Microneedle Unit

Steps 1 to 3. Manufacturing of Microneedle

The microneedle having the same shape as that of Example 1 was obtained by the same steps as Steps 1 to 3 of Example 1. The thickness of the substrate was 200 µm, the length of the projection was 200 µm, and the outline of the substrate was a circle with a diameter of φ12 mm.

Step 4. Production of Adhesive Sheet

The adhesive sheet having the same shape as that of Example 1 was obtained by the same step as Step 4 of Example 1. The thickness of the adhesive sheet was 200 µm, and the size of the adhesive sheet was 20 mm×20 mm square.

Step 5. Production of Protective Sheet

The protective sheet having the same configuration as that of the Example 1 except for the thickness was produced by the same step as Step 5 of Example 1. The thickness of the protective sheet was 300 µm, the opening was a circular region with a diameter of φ13 mm, the window was a rectangular region having a size of 10 mm×10 mm square, and the size of the protective sheet was 30 mm×30 mm square.

Steps 6 and 7. Bonding of Adhesive Sheet, Microneedle and Protective Sheet

The microneedle was bonded to the adhesive sheet, and the protective sheet was bonded to the adhesive region of the adhesive sheet by the same steps as Steps 6 and 7 of Example 1. Thus, the microneedle unit of Example 2 was obtained.

In the microneedle unit of Example 2, the adhesive region of 5×5 mm square on the adhesive surface of the adhesive sheet was exposed from the window of the protective sheet. The exposed region in the adhesive sheet had a maximum length of 7.1 mm.

Evaluation Result

The protective sheet was easily peeled off from the adhesive sheet by picking the protective sheet near the exposed region by using the thumb and forefinger of the right hand while picking the adhesive sheet including the exposed region by using the thumb and forefinger of the left hand. However, when picking the protective sheet by the right hand, the projection of the microneedle was slightly touched.

Example 3

Manufacturing of Microneedle Unit

Steps 1 to 3. Manufacturing of microneedle

The microneedle having the same shape as that of Example 1 was obtained by the same steps as Steps 1 to 3 of Example 1. The thickness of the substrate was 200 µm, the length of the projection was 200 µm, and the outline of the substrate was a circle with a diameter of φ12 mm.

Step 4. Manufacturing of adhesive sheet

The adhesive sheet having the same configuration as that of the Example 1 was produced by the same step as Step 4 of Example 1. The thickness of the adhesive sheet was 200 µm, and the size of the adhesive sheet was 20 mm×20 mm square.

Step 5. Manufacturing of Protective Sheet

The protective sheet having the same configuration as that of the Example 1 except for the size of the window was produced by the same step as Step 5 of Example 1. The thickness of the protective sheet was 600 µm, the opening was a circular region with a diameter of φ13 mm, the window was a rectangular region having a size of 6 mm×6 mm square, and the size of the protective sheet was 30 mm×30 mm square.

Steps 6 and 7. Bonding of Adhesive Sheet, Microneedle and Protective Sheet

The microneedle was bonded to the adhesive sheet, and the protective sheet was bonded to the adhesive region of the adhesive sheet by the same steps as Steps 6 and 7 of Example 1. Thus, the microneedle unit of Example 3 was obtained.

In the microneedle unit of Example 3, the adhesive region of 1×1 mm square on the adhesive surface of the adhesive sheet was exposed from the window of the protective sheet. The exposed region in the adhesive sheet had a maximum length of 1.4 mm.

Evaluation Result

An attempt was made to pick a portion of the protective sheet near the exposed region by using the thumb and forefinger of the right hand while picking the adhesive sheet including the exposed region by using the thumb and forefinger of the left hand. However, picking was difficult due to the small exposed region. Then, the nail was pressed against the adhesive sheet to form a starting point for peeling at a position near the end of the exposed region, and the protective sheet was peeled from the adhesive sheet. In comparison with Comparative example, the starting point for peeling was easily formed, the protective sheet was easily peeled, and the adhesive sheet was not deformed. However, in comparison with Examples 1 and 2, peeling of the protective sheet was difficult.

According to the above Examples and Comparative example, it was found that peeling of the protective sheet was easier in Examples 1 to 3 in which the adhesive sheet had the exposed region than in Comparative example in which the exposed region was not formed. Further, it was found that peeling of the protective sheet was easier in Example 1 in which the maximum length of the exposed region was 7 mm or more than in Example 3 in which the maximum length of the exposed region was less than 7 mm. Moreover, it was found that the protective function of the projections was higher in Example 1 in which the thickness of the protective sheet was larger than the length of the microneedle than in Example 2 in which the thickness of the protective sheet was smaller than the length of the microneedle.

According to one example use of a microneedle, a microneedle unit which includes a microneedle, an adhesive sheet and a protective sheet is used. The adhesive sheet has an adhesive surface and is attached to the substrate so that a portion of the adhesive surface is exposed at the outside of the substrate of the microneedle. The protective sheet protects the entire surface of the exposed portion of the adhesive surface. In use of the microneedle, the projection is pierced into the administration target after the protective sheet is peeled off from the adhesive surface, and the exposed adhesive surface is attached to the administration target. Accordingly, the microneedle is held at a desired position on the administration target while the projection is pierced into the administration target.

In order to avoid deterioration of functions of the microneedle unit such as a piercing function of the projection or an adhesive function of the adhesive sheet, it is preferable to avoid an excessively large force from acting on each part of the microneedle unit when the protective sheet is peeled off, that is, smooth peeling of the protective sheet is preferable. Accordingly, there is a need for a microneedle unit that enables easy peeling of a protective sheet.

An aspect of the present invention is to provide a microneedle unit that enables easy peeling of a protective sheet.

A microneedle unit for solving the above problem includes: a microneedle including a substrate having a first surface and a second surface which is a surface opposite from the first surface, and a projection protruding from the first surface of the substrate; an adhesive sheet including a sticking region attached to the second surface of the substrate, and an adhesive region which protrudes outside the substrate from the sticking region in a direction parallel to the second surface; and a protective sheet which covers a portion of the adhesive region at an outside of the substrate in the direction parallel to the second surface.

According to the above configuration, the protective sheet is easily peeled off compared with the configuration in which the adhesive region is entirely covered by the protective sheet since a starting point for peeling the protective sheet is easily formed at a position near a region exposed from the protective sheet in the adhesive region.

In the above configuration, a region exposed from the protective sheet in the adhesive region is preferably smaller than a region covered by the protective sheet.

According to the above configuration, since more than half of the adhesive region is covered by the protective sheet, an excessive decrease in protective function of the adhesive region due to the protective sheet can be avoided while achieving easy peeling of the protective sheet.

In the above configuration, the protective sheet preferably includes: a first opening from which the projection of the microneedle is exposed; and a second opening from which a portion of the adhesive region is exposed.

According to the above configuration, since a portion of the adhesive region is exposed from the second opening formed in the protective sheet, a region from which the protective sheet is exposed can be easily provided in the adhesive region.

In the above configuration, the adhesive region includes an exposed region exposed from the protective sheet, wherein a length of the longest line segment among the line segments connecting any two points on an outer peripheral edge of the exposed region and extending through the exposed region is preferably 7 mm or more.

According to the above configuration, a region exposed from the protective sheet may have a size that can be supported by a center portion of a human finger. Accordingly, when peeling the protective sheet, a user of the microneedle unit can easily peel the protective sheet off by supporting the region exposed from the protective sheet by hand.

In the above configuration, a thickness of the protective sheet is preferably larger than a length of the microneedle in a thickness direction of the substrate.

According to the above configuration, the top surface of the protective sheet is located higher than the tip of the projection, thereby preventing the projection from being touched by a human hand or other members. Further, the microneedle units can be stacked in the thickness direction of the protective sheet without damaging the projections even if the projections 12 are not protected by another member. Accordingly, the microneedle unit can be easily handled and managed.

According to embodiments of the present invention, the protective sheet can be easily peeled off in the microneedle unit.

REFERENCE SIGNS LIST

10 . . . microneedle, 11 . . . substrate, 11S . . . first surface, 11T . . . second surface, 12 . . . projection, 20 . . . microneedle unit, 21 . . . adhesive sheet, 21S . . . adhesive surface, 22 . . . protective sheet, 23 . . . opening, 24 . . . window, 25 ... weakened portion, 30 ... protective film, 40 ... case, M1 ... sticking region, M2 ... adhesive region, N1 ... covered region, N2 ... exposed region Obviously, numerous modifications and variations of the present invention are possible in light of the above teachings. It is therefore to be understood that within the scope of the appended claims, the invention may be practiced otherwise than as specifically described herein.

What is claimed is:

1. A microneedle unit, comprising:
   a microneedle comprising a substrate and a projection protruding from a first surface of the substrate;
   an adhesive sheet attached to a second surface of the substrate on an opposite side with respect to the first surface such that the substrate is positioned on a sticking region of the adhesive sheet and that the adhesive sheet has an adhesive region outside the sticking region; and
   a protective sheet adhered to the adhesive region of the adhesive sheet and having a first opening such that the first opening is exposing the microneedle on the adhesive sheet and that the protective sheet has a thickness that is larger than a sum of a thickness of the substrate and a length of the projection in a thickness direction of the substrate,
   wherein the adhesive sheet has an adhesive surface having the sticking region and the adhesive region outside the sticking region such that the microneedle and the protective sheet are adhered to the adhesive surface of the adhesive sheet and that the microneedle is positioned inside the first opening of the protective sheet.

2. The microneedle unit of claim 1, wherein the adhesive region has an exposed region which is exposed from the protective sheet and has an area smaller than an area covered by the protective sheet.

3. The microneedle unit of claim 1, wherein the protective sheet includes a second opening which exposes a portion of the adhesive region.

4. The microneedle unit of claim 2, wherein the protective sheet includes a second opening which exposes a portion of the adhesive region.

5. The microneedle unit of claim 1, wherein the adhesive region includes an exposed region exposed from the protective sheet, and the adhesive region is formed such that a longest line segment among line segments which connect any two points on an outer peripheral edge of the exposed region and pass through the exposed region has a length of 7 mm or more.

6. The microneedle unit of claim 2, wherein the adhesive region is formed such that a longest line segment among line segments which connect any two points on an outer peripheral edge of the exposed region and pass through the exposed region has a length of 7 mm or more.

7. The microneedle unit of claim 3, wherein the adhesive region includes an exposed region exposed from the protective sheet, and the adhesive region is formed such that a longest line segment among line segments which connect any two points on an outer peripheral edge of the exposed region and pass through the exposed region has a length of 7 mm or more.

8. The microneedle unit of claim 1, wherein the microneedle has the projection formed in a plurality such that the plurality of projections is formed on the first surface of the substrate.

9. The microneedle unit of claim 2, wherein the microneedle has the projection formed in a plurality such that the plurality of projections is formed on the first surface of the substrate.

10. The microneedle unit of claim 3, wherein the microneedle has the projection formed in a plurality such that the plurality of projections is formed on the first surface of the substrate.

11. The microneedle unit of claim 5, wherein the microneedle has the projection formed in a plurality such that the plurality of projections is formed on the first surface of the substrate.

12. The microneedle unit of claim 1, wherein the protective sheet has a weakened portion such that the protective sheet is foldable at the weakened portion toward a side opposite to the adhesive sheet.

13. The microneedle unit of claim 9, wherein the protective sheet has a weakened portion such that the protective sheet is foldable at the weakened portion toward a side opposite to the adhesive sheet.

14. The microneedle unit of claim 10, wherein the protective sheet has a weakened portion such that the protective sheet is foldable at the weakened portion toward a side opposite to the adhesive sheet.

15. The microneedle unit of claim 11, wherein the protective sheet has a weakened portion such that the protective sheet is foldable at the weakened portion toward a side opposite to the adhesive sheet.

16. The microneedle unit of claim 1, further comprising:
    a protective film positioned on the protective sheet on a side opposite to the adhesive sheet such that the protective film covers the first opening over the microneedle.

17. The microneedle unit of claim 13, further comprising:
    a protective film positioned on the protective sheet on a side opposite to the adhesive sheet such that the protective film covers the first opening over the microneedle.

18. The microneedle unit of claim 14, further comprising:
    a protective film positioned on the protective sheet on a side opposite to the adhesive sheet such that the protective film covers the first opening over the microneedle.

19. The microneedle unit of claim 15, further comprising:
    a protective film positioned on the protective sheet on a side opposite to the adhesive sheet such that the protective film covers the first opening over the microneedle.

20. The microneedle unit of claim 1, wherein the microneedle is a molded product having a first portion forming the substrate and a second portion forming the projection.

* * * * *